United States Patent [19]

Thompson et al.

[11] 4,184,374

[45] Jan. 22, 1980

[54] ULTRASONIC INSPECTION OF A CYLINDRICAL OBJECT

[75] Inventors: Robert B. Thompson; Christopher M. Fortunko, both of Thousand Oaks, Calif.

[73] Assignee: Rockwell International Corporation, El Segundo, Calif.

[21] Appl. No.: 918,204

[22] Filed: Jun. 22, 1978

[51] Int. Cl.² .......................................... G01N 29/04
[52] U.S. Cl. ...................................... 73/640; 73/643
[58] Field of Search ................. 73/643, 640, 638, 637, 73/622; 324/228, 239, 240, 241, 242, 243

[56] References Cited

U.S. PATENT DOCUMENTS

| | | | |
|---|---|---|---|
| 3,555,887 | 1/1971 | Wood | 73/643 |
| 3,763,695 | 10/1973 | Zeiters | 73/638 |
| 3,850,028 | 11/1974 | Thompson et al. | 73/643 |
| 4,092,868 | 6/1978 | Thompson et al. | 73/643 |
| 4,100,809 | 7/1978 | Bobrov et al. | 73/643 |

*Primary Examiner*—Stephen A. Kreitman
*Attorney, Agent, or Firm*—L. Lee Humphries; Craig O. Malin; John J. Deinken

[57] ABSTRACT

A method and an apparatus are provided for ultrasonically inspecting a cylindrical object. The object is placed between the poles of a magnet to create a circumferential magnetic field in the object. A group of electromagnetic transducers (EMAT's) are placed adjacent the material so that the transducers scan the entire object when it is rotated. When an RF signal is applied to the transducers, elastic waves are generated in the material. These elastic waves reflect from defects in the material and these reflections are received by the transducers.

12 Claims, 8 Drawing Figures

ULTRASONIC INSPECTION OF A CYLINDRICAL OBJECT

STATEMENT OF GOVERNMENT INTEREST

The Invention herein described was made in the course of or under a contract or subcontract thereunder, (or grant) with the Department of the Army.

BACKGROUND OF THE INVENTION

1. Field of the Invention

This invention relates to the field of inspection, particularly to ultrasonic inspection of metal parts.

2. Description of the Prior Art

Conventional ultrasonic inspection equipment and methods utilize piezoelectric crystals for injecting a narrow beam of elastic waves into the part being inspected. Such transducers do not lend themselves to rapid inspection of high production parts because they must be moved along the surface of the part in tight contact with the part. In some cases, water can be used as a medium for conducting waves from the transducer into the part. However, such technique is still not suitable for the complete inspection of cylindrical objects under high speed conditions.

More recently, non-contact electromagnetic transducers (commonly called EMAT's) have been developed which utilize the interaction between a static magnetic field and an induced eddy current in the material being inspected to create dynamic forces in the material. On such electromagnetic transducer is the meander coil transducer described in U.S. Pat. No. 3,850,028.

EMAT's can be used in a manner similar to the earlier developed piezoelectric transducer by placing the transducer against a stationary part. However, a need exists for more rapid automatic inspection of parts, particularly for the inspection of high production parts such as artillery shells, vehicle parts, and other mass produced items. Until the present invention, EMAT's have not found extensive use for inspection of mass produced parts, because apparatus and methods taking advantage of their special features have not been available.

SUMMARY OF THE INVENTION

It is an object of the invention to provide a method and an apparatus for automatically inspecting cylindrical objects.

It is an object of the invention to provide a method and an apparatus for ultrasonically inspecting cylindrical objects utilizing a noncontact transducer.

It is an object of the invention to provide a method and apparatus suitable for use in a production line for rapidly inspecting objects having a substantially cylindrical cross section.

According to the invention, the object to be inspected is placed between the poles of a magnet to create a circumferential magnetic field in the object. A group of electromagnetic transducers (EMAT's) are placed adjacent to the material so that the transducers scan the entire object when it is rotated. When an RF signal is applied to the transducers, elastic waves are generated in the material. These elastic waves reflect from defects in the material and these reflections are received by the transducers.

These and other objects and features of the present invention will be apparent from the following detailed description, taken with reference to the accompanying drawings.

DESCRIPTION OF THE PREFERRED EMBODIMENT

Figure 1:
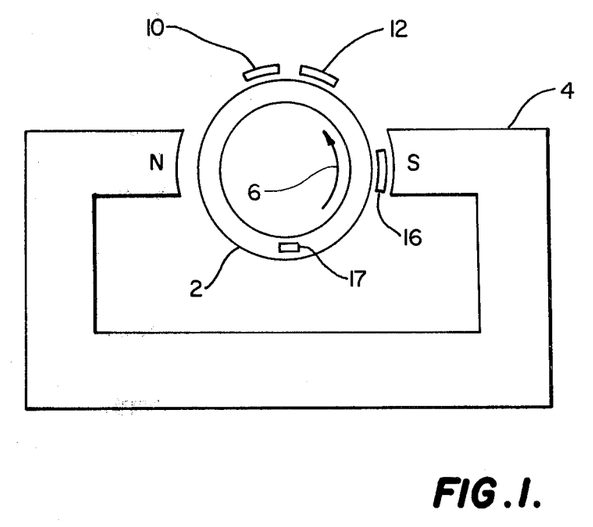
FIG. 1 is an end view showing the position of the object being tested with respect to the magnet.

FIG. 1 is a schematic end view illustrating the inspection set-up with respect to cylindrical part 2 being inspected. Cylindrical part 2 is positioned between the north and south poles of a large magnet 4 so that it can be rotated as shown by arrow 6. Transmitting electromagnetic transducer (EMAT) 10 and receiving EMAT 12 are placed close to the circumference of part 2.

Figure 2:
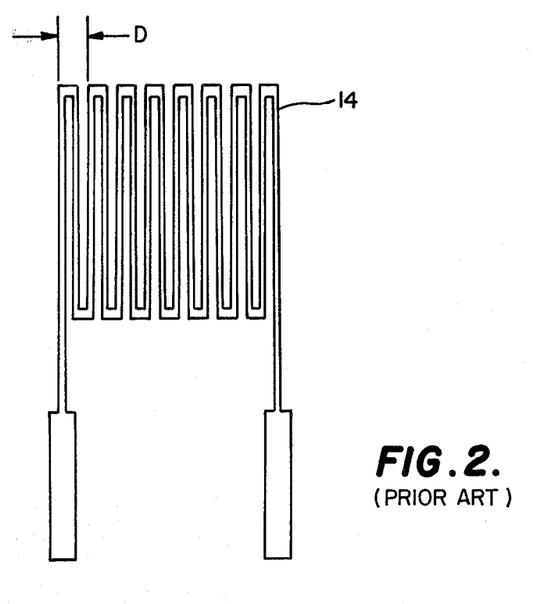
FIG. 2 is a plan view of a meander coil used in the EMAT.

EMAT transducers 10, 12 consist of a small meander coil 14 having a period, D, such as shown in FIG. 2. When a current is passed through coil 14, eddy currents are created in part 2 (provided that part 2 is electrically conductive) and these interact with the static field from magnet 4 to create forces in part 2 based upon the known Lorentz force mechanism. If part 2 is ferromagnetic, then magnetic fields are created in part 2 by the current in coil 14. These magnetic fields can generate waves by the mechanism of magnetostriction. In fact, for an electrically conductive ferromagnetic material such as steel, magnetostriction is the dominant wave-creating mechanism. However, EMATs using either or both mechanism are suitable for the invention. These forces (Lorentz or magnetostrictive) can launch different types of elastic waves (ultrasonic waves) in part 2, including surface waves and bulk shear waves.

Surfaces waves (Rayleigh waves) are launched into part 2 when the frequency, f, of the current in coil 14 is chosen according to the relation:

$$fD = V_R,$$

where D is the period of coil 14 and $V_R$ is the surface wave velocity. Surfaces waves are efficiently generated at frequency f because their wavelength is then equal to coil period D.

Angle shear waves are generated by coil 14 at higher frequencies, since the shorter wavelength can still match the coil period when the shear wave is traveling at an angle into the material. This angle, measured with respect to surface normal, is given by the relation:

$$V = \sin^{-1}(V_s/fD),$$

where $V_s$ is the shear wave velocity.

Both surface waves and angle shear waves can be used in the invention depending upon the configuration of the part being inspected and upon the type of defect being revealed. Unlike surface waves, angle shear waves can be used to find defects on either the surface adjacent the transducer (the O.D. surface of part 2) or the surface opposite the transducer (the I.D. surface of part 2).

As shown in FIG. 1, EMAT's 10 and 12 are positioned away from the poles of magnet 4 in a region where the flux is traveling circumferentially with part 2. When coil 14 of EMAT 10 is oriented at right angles to the circumferential magnetic field, the elastic waves generated and received by EMAT's 10, 12 travel circumferentially in part 2. However, elastic waves can be launched in different directions within part 2 if an EMAT is placed directly under a pole in the space between the pole and part 2 as shown in FIG. 1 for EMAT 16. In this location, the flux is entering part 2 in a predominantly radial direction. Thus, coil 14 in EMAT 16 can be oriented in any direction and still efficiently launch and receive elastic wave because it is always at right angles to a normal field.

EMAT 17 is placed on a radial surface or base of part 2. In this location it can be used to inspect the outer surface of the base when operated to generate surface waves, or used to inspect the interior of the wall in the base region using angle shear waves.

Figure 3:
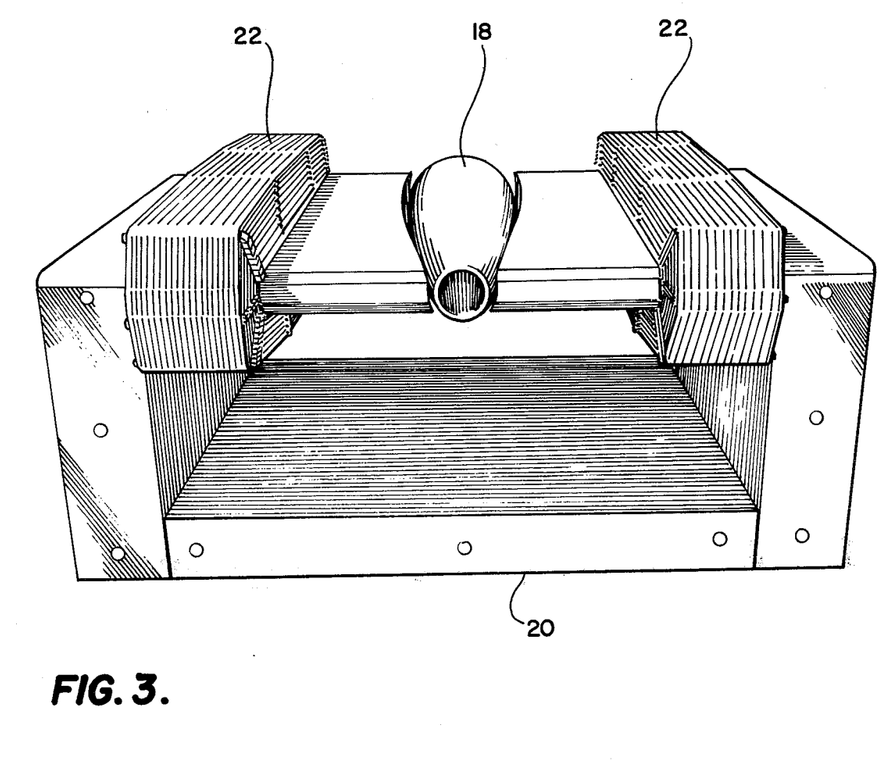
FIG. 3 is a perspective view of an electromagnet with a shell in the inspection position.

In a preferred embodiment, the part being inspected is an artillery shell 18 and the magnet used to provide the field is an electromagnet 20 such as shown in FIG. 3. Individual turns of coils 22 of electromagnet 20 are spaced apart so as to provide air cooling.

Figure 4:
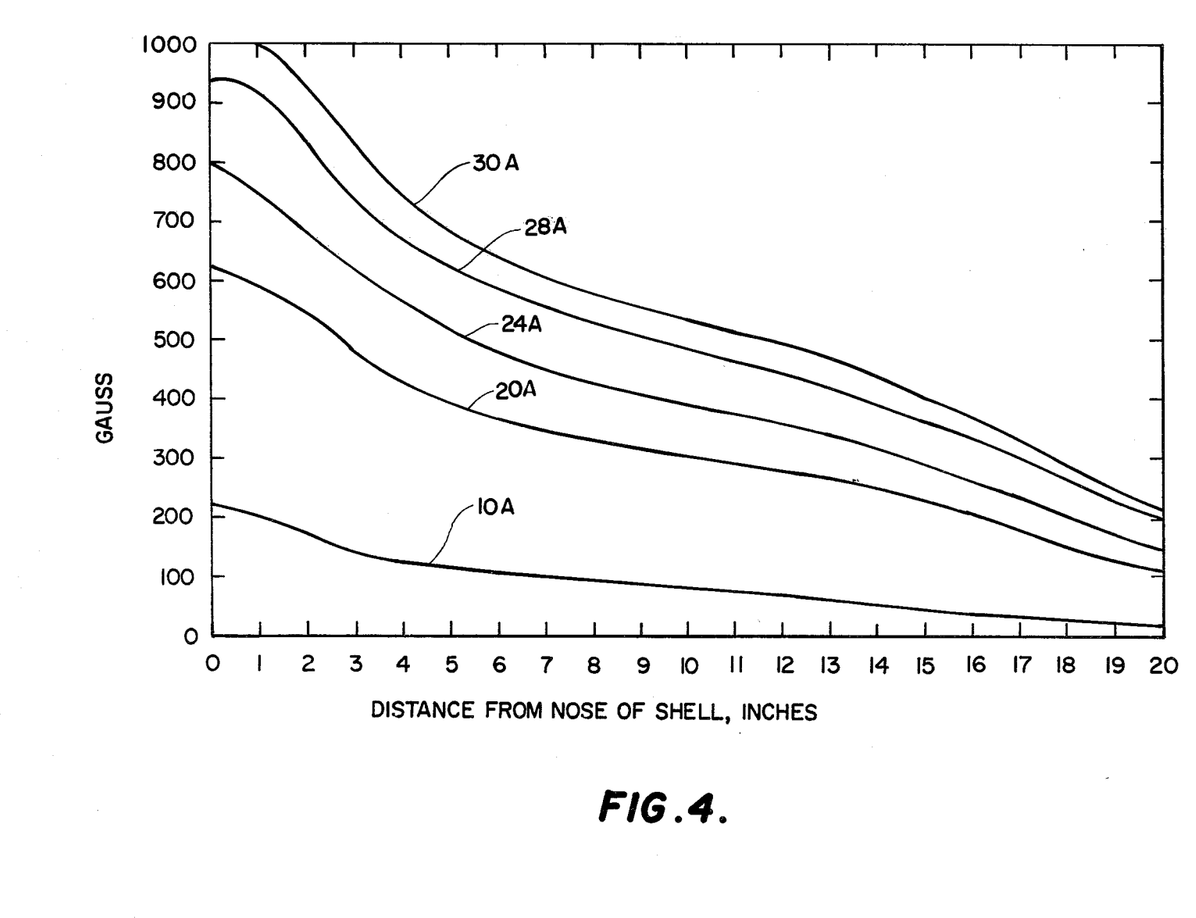
FIG. 4 is a plot of the circumferential field strength vs. location along the length of the shell shown in FIG. 3.
Figure 5:
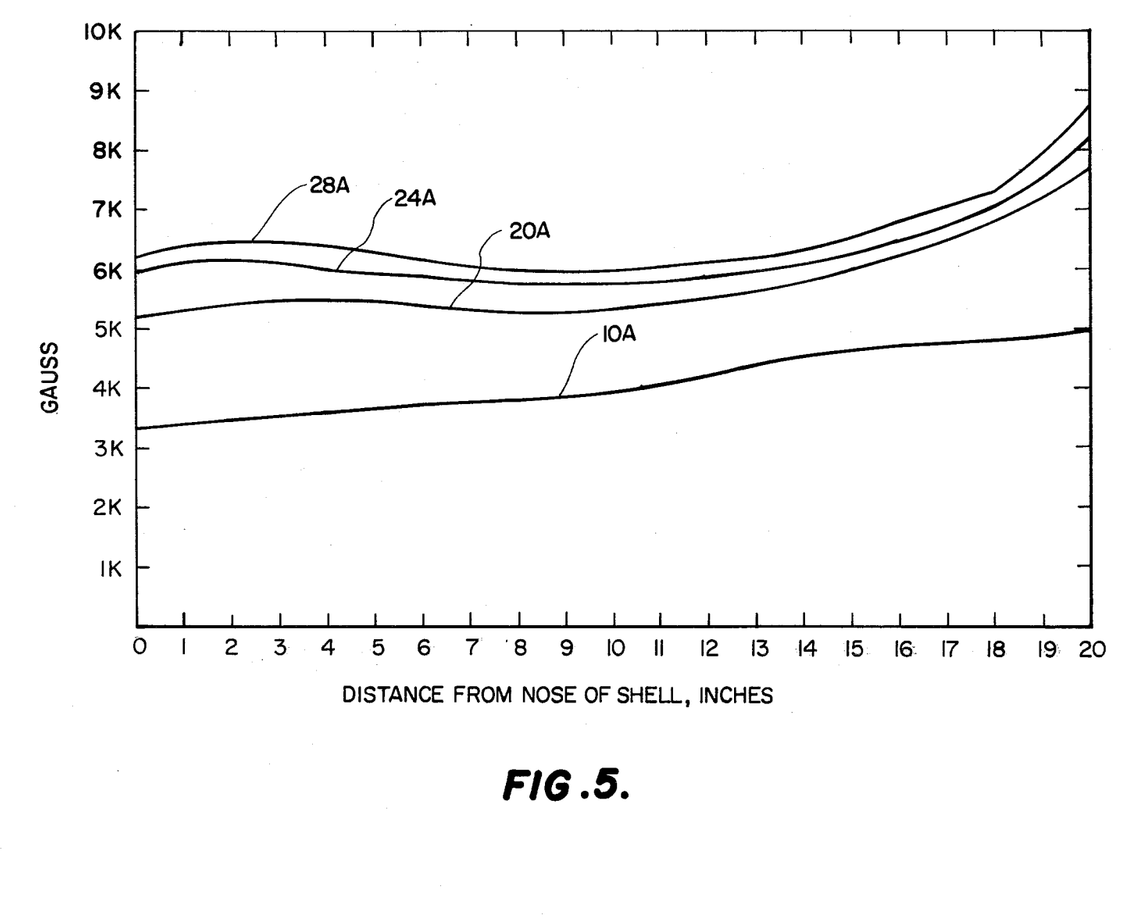
FIG. 5 is a plot of the normal field strength vs. location along the length of the shell shown in FIG. 3.

FIGS. 4 and 5 show the strength of magnetic fields obtained in the circumferential position (for EMATs 10, 12) and in the radial position (for EMAT 16), respectively, at several coil currents for a particular artillery shell. The flux density varies along the length of the shell because the wall thickness of the shell varies. Optimum flux density can be obtained at each location by varying the thickness of the magnet's pole pieces or by changing the air gap in a known manner.

For iron base alloys, a field strength of 300 gauss provides good transducer efficiency. It was discovered in tests leading to the present invention that there is a large peak in transducer efficiency at 300 gauss caused by magnetostriction. A field strength of only 300 gauss was shown to produce signals as large as are obtained at a field strength of 10,000 gauss. The current furnished to coils 22 and the pole piece configuration can be readily adjusted to provide the flux necessary to take advantage of the high efficiency provided by this magnetostrictive effect.

Figure 6:
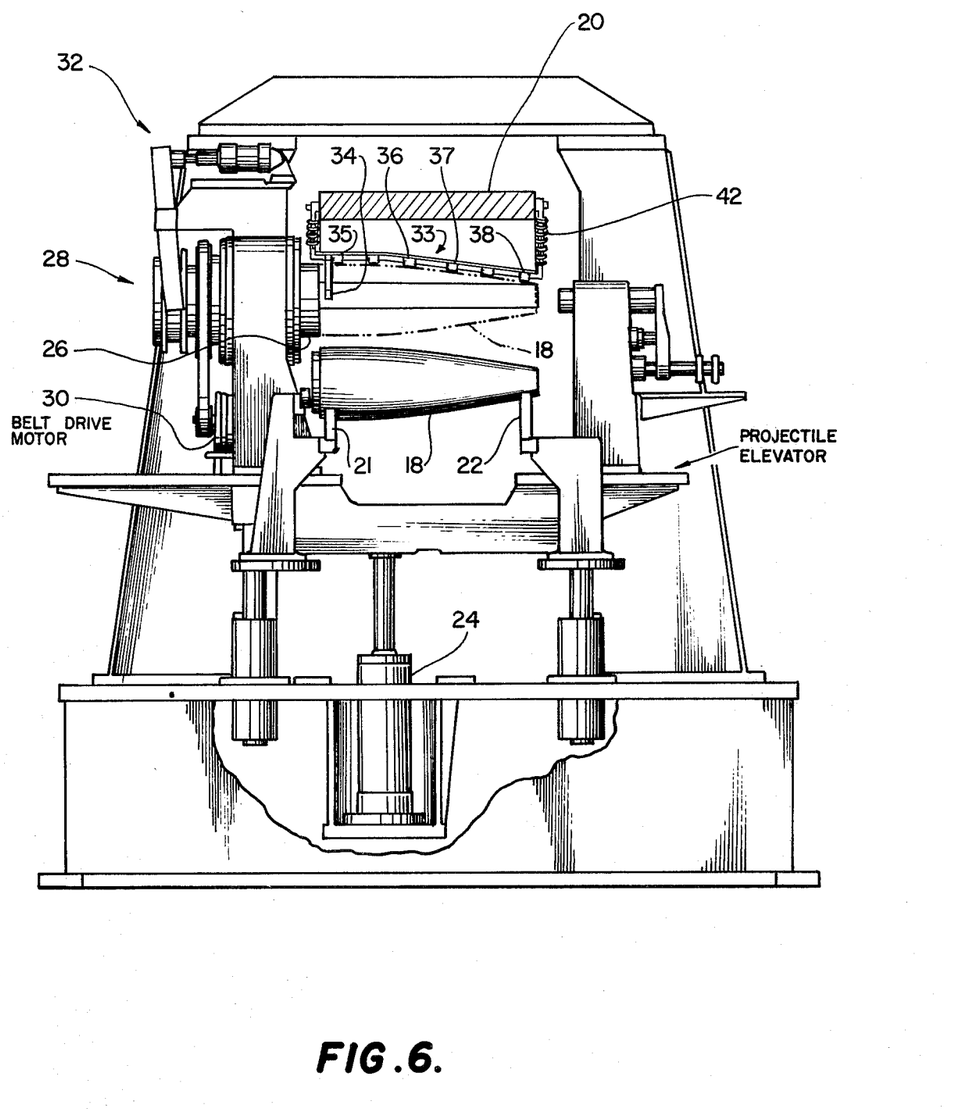
FIG. 6 is an elevation view of an inspection station.

An inspection station for ultrasonically inspecting artillery shells 18 is shown in FIG. 6. This station is part of a production line and is positioned in the line after a dimensional inspection station and before a threading operation. The shells are held in V-blocks 921, 22 and moved from station to station utilizing a walking-beam movement. When shell 18 reaches its position in the station, hydraulic cylinder 24 raises the projectile to a position between the poles of electromagnet 20 as shown by the dashed lines in FIG. 6.

Electromagnet 20 shown in FIG. 6 is the same as electromagnet 20 shown in FIG. 3 except that it has been turned upside down so that projectile 18 can be inserted into the air gap from below. Additionally for clarity, the electromagnet has been sectioned longitudinally along the center of the air gap and the coil has been omitted.

When shell 18 is in the inspection position as shown by the dashed lines, it is held at its base in a hollow chuck 26 which is part of a belt driven rotating drive 28 which includes electric drive motor 30 and spin detector 32. The shell can then be rotated while it is scanned by ultrasonic waves. After ultrasonic inspection, hydraulic cylinder 24 moves upward to receive shell 18 in V-blocks 21, 22 and a walking beam mechanism removes shell 18 from the station.

In order to accurately scan the entire shell, a group of EMATs 34–38 are supported on rack 33 which is placed adjacent or against shell 18. Although the individual coils 14 of each EMAT 34–38 need not touch shell 18, it is advantageous in most cases to have rack 34 bear against shell 18 so that the coils in each EMAT are spaced a fixed distance from shell 18 at all times, even though there may be some eccentricity in shell 18 or in rotating drive 28. Rack 33, or even individual EMATs 34–38, can be spring mounted 42 so as to bear against shell 18 with a constant load. EMAT 34 is used to locate circumferentially oriented defects on the ID and OD using angle shear waves and EMATs 35–38 are used to inspect the ID and OD of the bourrelet and ogive regions for longitudinally oriented defects using angle shear waves.

To inspect the base of projectile 18, a second rack (not shown) extends through hollow chuck 28 and is used to position two EMATs adjacent the base (a radial face) of projectile 18. One of these two base EMATs is used to inspect the outer surface of the base using surface waves, and the other base EMAT is used to inspect the interior of the wall in the base region using angle shear waves.

Figure 7:
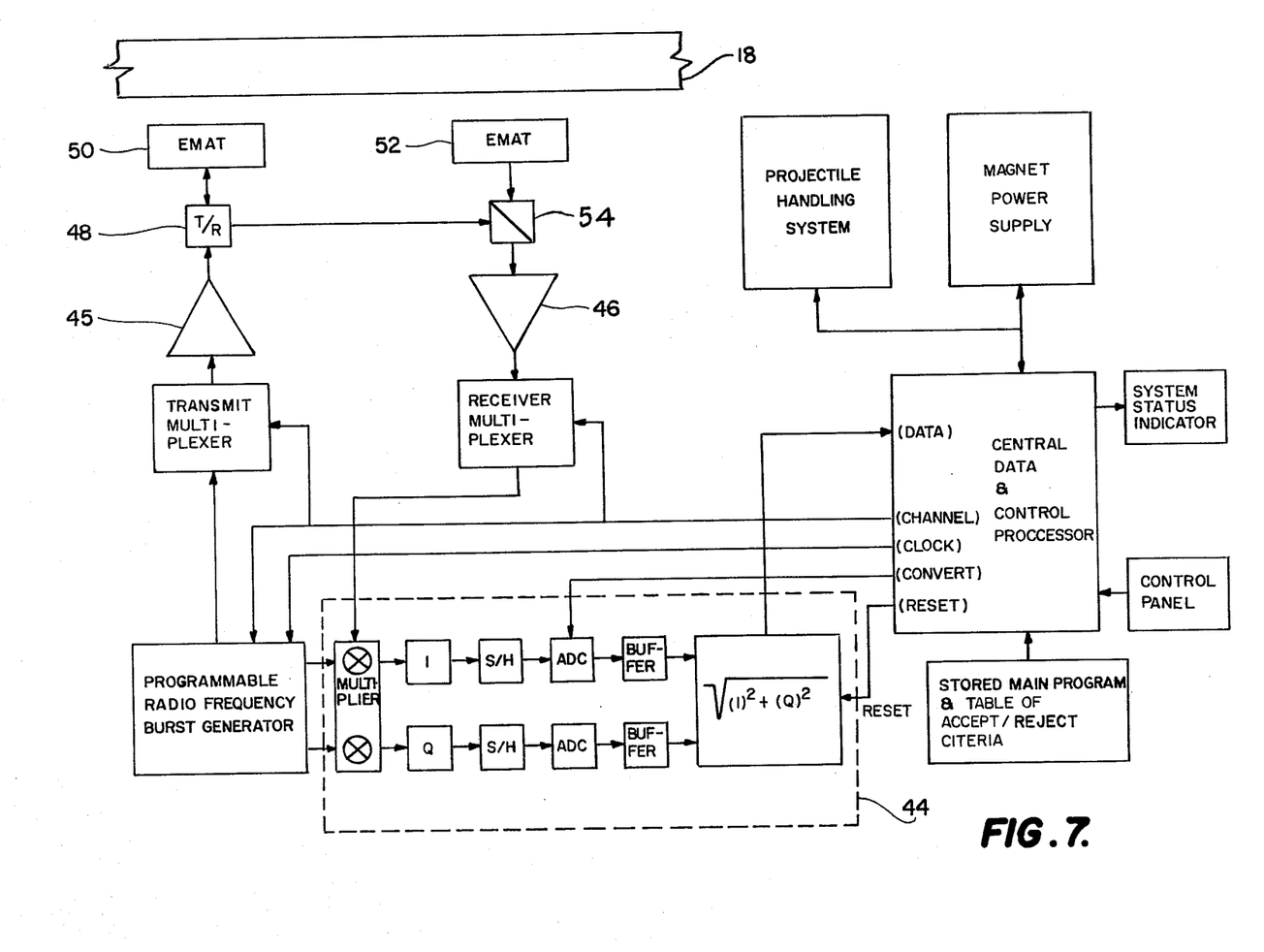
FIG. 7 is a block diagram of an electronic system for use with the inspection station.

FIG. 7 is a block diagram of a system for processing ultrasonic signals, controlling projectile handling machinery, and making accept-reject decisions. In this system, a correlation receiver 44 is used to achieve nearly matched filtering and demodulation of the received ultrasonic data. An advantage of this type receiver is that filtering of received data from all ultrasonic channels can be accomplished by the same receiver with uniform fidelity.

Other special features of the system are a non-linear power amplifier 45 for exciting the ultrasonic signals, an electrical matching network (not shown) for optimizing the noise figure of the receiver-preamplifier 46, and a transmit receiver circuit (T/R switch) 48 to protect the sensitive receiver electronics from overloading by the transmitter output signal.

The system shown in FIG. 7 can function in either a pulse echo mode using EMAT 50 as both a transmitter and a receiver, or in a pitch-catch mode using EMAT 50 as a transmitter and EMAT 52 as a receiver. Mode selector switch 54 is used to select the mode of operation.

Figure 8:
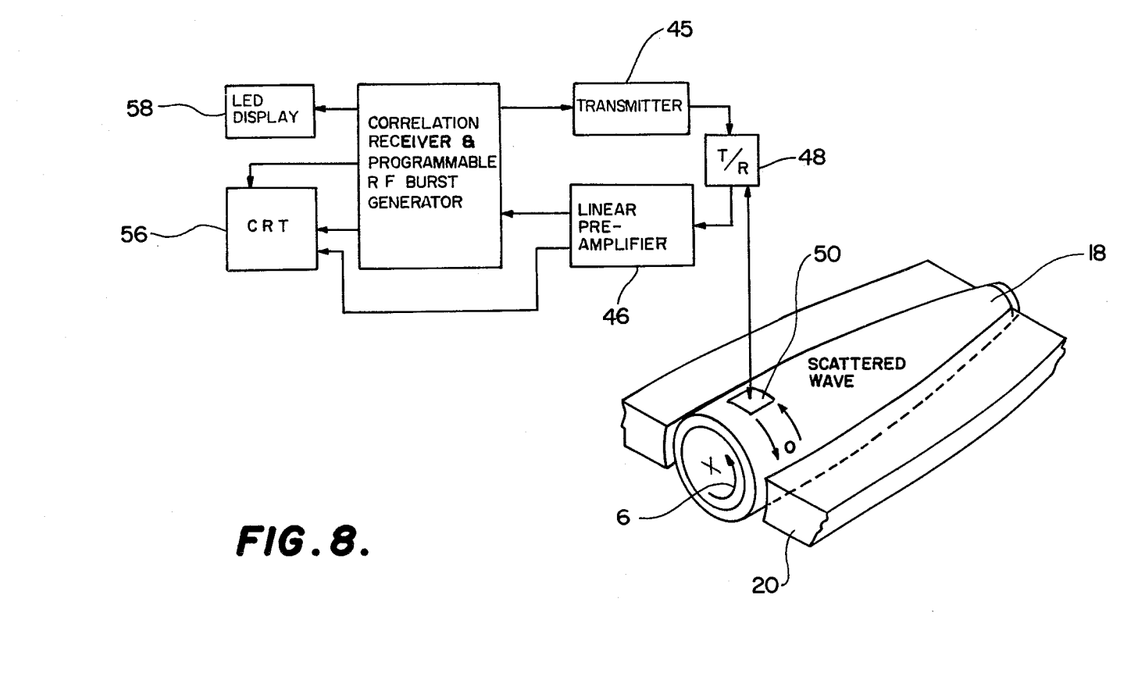
FIG. 8 is an experimental arrangement for evaluating the flaw-detecting ability of an EMAT and related electronics.

FIG. 8 shows an experimental set up for evaluating the ability of a single EMAT 50 to detect flaws in shell 18. Elements performing substantially the same functions as previously described are given the same reference numbers. A cathode ray tube 56 and a four digit LED panel 58 are used to illustrate the variety of waveforms involved in the signal processing and their interrelationships. The electronics package is tuned to a center frequency of approximately 1.8 MHz and electromagnetic transducer 50 is excited by a tone burst centered at this frequency and containing 8 cycles.

Electromagnetic transducer 50 is of the conventional meander coil geometry made by photo-etching a one ounce layer of copper deposited on a 0.0025 cm (0.001 in.) kapton substrate. A flexible black rubber pad is attached to the opposite side of the kapton substrate to help maintain conformity to the radius of curvature in the bourrelet region. The transducer coil contains eight full wave periods of 0.3 cm (0.120 in.) each and has an active acoustic aperture of 2.5 cm (1.00 in.). In addition, a 0.025 cm (0.010 in.) thick paper spacer was used as a wear plate to maintain a near constant separation between transducer 50 and the wall of shell 18.

Measurements using angle shear and horizontal waves were made to demonstrate the ability of the system to detect flaws in projectile 18. The experimental results are summarized in the table below which gives the relative position and orientations of the simulated defects as well as the peak-to-peak rf voltages of the received ultrasonic signatures. The RMS noise voltage level was approximately 0.007 Volts in all cases. All the defects shown in the table were on the outside surface of shell 18 except for the last two defects which were on the I.D. surface. For these I.D. defects, EMAT 50 was positioned in the air gap between a pole and shell 18 in the normal field.

| | DEFECT | | | REC'D SIGNAL |
|---|---|---|---|---|
| Distance fm. Base (Inches) | Surface Length (inches) | Max. Depth (inches) | Cant Angle w/respect to axis | Output Level (V) |
| 6.5 | .146 | .014 | 0 | 1.2 |
| 8 | .158 | .014 | 0 | 1.6 |
| 9.5 | .186 | .019 | 0 | 2 |
| 9.5 | .256 | .052 | 0 | 4 |
| 11 | .116 | .009 | 0 | .8 |
| 12.75 | .190 | .022 | 0 | 2.8 |
| 14.5 | .174 | .015 | 0 | 1.2 |
| 2 | .172 | .020 | 10 | .6 |
| 2 | .177 | .020 | 20 | .2 |
| 2 | .186 | .018 | 30 | .08 |
| 2 | .374 | .011 | 0 | 2.2 |
| 3.5 | .222 | .035 | 0 | 3.6 |
| 5 | .105 | .019 | 0 | 1.5 |
| 3 | .179 | .021 | 0 | 3 |
| 5 | .157 | .107 | 0 | 2 |
| 2 | .030 | — | 90 | .8 |
| 2 | .030 | — | 90 | .6 |

Numerous variations and modifications may be made without departing from the present invention. The type EMAT used, its shape, location, and orientation can be varied as necessary to inspect a particular part, provided only that a suitable eastic wave is electromagnetically generated in the part being inspected. Accordingly, it should be clearly understood that the form of the present invention described above and shown in the accompanying drawings is illustrative only and is not intended to limit the scope of the present invention.

What is claimed is:

1. A method of inspecting an object of substantially cylindrical cross section and of electrically conductive and/or ferromagnetic material, comprising the steps of:
   placing said object between a north pole and a south pole of a magnet to create a circumferential magnetic field in said object;
   placing at least one electromagnetic transducer adjacent said magnetic field in said material;
   passing an electrical signal through said transducer to generate elastic waves in said object;
   receiving reflections of said elastic wave as it travels in said object; and
   rotating said object relative to said transducer to scan said object under said transducer, whereby the existence of defects and discontinuities in said object are revealed by said reflections.

2. The method as claimed in claim 1, wherein said circumferential magnetic field extends along the entire length of said object.

3. The method as claimed in claim 2, wherein said magnet comprises an electromagnet.

4. The method as claimed in claim 2, wherein said magnet comprises a permanent magnet.

5. The method as claimed in claim 1, wherein said transducer is placed between one of said poles and a surface of said object where said magnetic field is substantially perpendicular to said surface.

6. The method as claimed in claim 1, wherein said transducer is placed at a location spaced from said poles along a surface of said object where said magnetic field is substantially parallel to said outside surface.

7. The method as claimed in claim 1, wherein said at least one electromagnetic transducer comprises a single electromagnetic transducer for both generating said elastic waves and for receiving said reflections.

8. The method as claimed in claim 1, wherein said at least one electromagnetic transducer comprises one electromagnetic transducer for generating said elastic waves and another electromagnetic transducer for receiving said reflections.

9. The method as claimed in claim 1, wherein said transducer comprises a meander coil.

10. The method as claimed in claim 1, wherein said transducer is placed on a radial face of said object.

11. An apparatus for inspecting an object of substantially cylindrical cross section of electrically conductive and/or ferromagnetic material, said apparatus comprising:
    a magnet having north and south poles;
    means for placing the object between said poles;
    at least one electromagnetic transducer positioned to be adjacent the surface of the object when the object is placed between said poles;
    means coupled to a transducer of said at least one electromagnetic transducer for supplying an electrical signal to said transducer;
    means coupled to a transducer of said at least one electromagnetic transducer for receiving reflections of elastic waves; and
    means couplable to the object for rotating the object when it is placed between said poles.

12. The apparatus as claimed in claim 11, wherein said transducer comprises a group of transducers positioned along the object so that the object is scanned by said group of transducers when the object is rotated.

* * * * *